(12) United States Patent
Giraud et al.

(10) Patent No.: US 11,617,842 B2
(45) Date of Patent: Apr. 4, 2023

(54) INHALER AND METHODS OF USING AND MAKING THE SAME

(71) Applicants: CSP TECHNOLOGIES, INC., Auburn, AL (US); SIMPLIFIED SOLUTIONS SWEDEN AB, Lindome (SE)

(72) Inventors: Jean-Pierre Giraud, Auburn, AL (US); Bruce Rabinne, Boissy-le-Chatel (FR); Yutaka Kataoka, Lindome (SE)

(73) Assignee: CSP Technologies, Inc., Auburn, AL (US)

( * ) Notice: Subject to any disclaimer, the term of this patent is extended or adjusted under 35 U.S.C. 154(b) by 791 days.

(21) Appl. No.: 16/494,388

(22) PCT Filed: Mar. 15, 2018

(86) PCT No.: PCT/US2018/022732
§ 371 (c)(1),
(2) Date: Sep. 16, 2019

(87) PCT Pub. No.: WO2018/170315
PCT Pub. Date: Sep. 20, 2018

(65) Prior Publication Data
US 2020/0129712 A1    Apr. 30, 2020

Related U.S. Application Data

(60) Provisional application No. 62/471,661, filed on Mar. 15, 2017, provisional application No. 62/514,072, filed on Jun. 2, 2017.

(51) Int. Cl.
*A61M 15/00*    (2006.01)

(52) U.S. Cl.
CPC .............. *A61M 15/0043* (2014.02); *A61M 15/0021* (2014.02); *A61M 15/0048* (2014.02);
(Continued)

(58) Field of Classification Search
CPC .............. A61M 15/00; A61M 15/0001; A61M 15/0021; A61M 15/0025; A61M 15/0026;
(Continued)

(56) References Cited

U.S. PATENT DOCUMENTS

| 5,911,937 A | 6/1999 | Hekel |
| 5,988,163 A | 11/1999 | Casper et al. |

(Continued)

FOREIGN PATENT DOCUMENTS

| CN | 1555277 A | 12/2004 |
| EP | 2712643 A1 | 4/2014 |

(Continued)

*Primary Examiner* — Colin W Stuart
(74) *Attorney, Agent, or Firm* — Mark T. Vogelbacker; Eckert Seamans Cherin & Mellott, LLC

(57) ABSTRACT

A dose ring for a dry powder inhaler (DPI) device includes an aluminum foil member covering particulate medication cavities and through holes. The device includes hinged flaps formed by a cut so that one radial side is uncut and forms a hinge. Each flap can cover both a cavity for particulate medication and a through hole located between that cavity and the circular inside edge of the dose ring.

20 Claims, 13 Drawing Sheets

(52) U.S. Cl.
    CPC ..... *A61M 15/0075* (2014.02); *A61M 15/0026* (2014.02); *A61M 15/0091* (2013.01); *A61M 2202/062* (2013.01); *A61M 2202/064* (2013.01)

(58) Field of Classification Search
    CPC ............ A61M 15/0028; A61M 15/003; A61M 15/0043; A61M 15/0045; A61M 15/0046; A61M 15/0048; A61M 15/0091; A61M 2202/062; A61M 2202/064
    See application file for complete search history.

(56) References Cited

U.S. PATENT DOCUMENTS

| | | | |
|---|---|---|---|
| 6,080,350 | A | 6/2000 | Hekel |
| 6,124,006 | A | 9/2000 | Hekel |
| 6,130,263 | A | 10/2000 | Hekel |
| 6,194,079 | B1 | 2/2001 | Hekel et al. |
| 6,214,255 | B1 | 4/2001 | Hekel |
| 6,486,231 | B1 | 11/2002 | Hekel |
| 6,810,872 | B1 | 11/2004 | Ohki et al. |
| 6,871,647 | B2 | 3/2005 | Allan et al. |
| 7,005,459 | B2 | 2/2006 | Hekel |
| 7,401,713 | B2 | 7/2008 | Ede et al. |
| 8,297,277 | B2 | 10/2012 | Rohrschneider et al. |
| 8,424,518 | B2 | 4/2013 | Smutney et al. |
| 9,095,670 | B2 | 8/2015 | Briant et al. |
| 9,211,383 | B2 | 12/2015 | Kjellgren et al. |
| 9,987,440 | B2 * | 6/2018 | Åberg ............... A61M 15/0016 |
| 9,993,601 | B2 | 6/2018 | Jung et al. |
| 10,124,130 | B2 | 11/2018 | Houzego et al. |
| 10,201,672 | B2 | 2/2019 | Smutney et al. |
| 10,751,488 | B2 | 8/2020 | Smutney et al. |
| 2009/0084379 | A1 | 4/2009 | Goeckner et al. |
| 2010/0078022 | A1 | 4/2010 | Striebig et al. |
| 2011/0259326 | A1 | 10/2011 | Briant et al. |
| 2014/0007875 | A1 | 1/2014 | Aaberg et al. |
| 2014/0174441 | A1 * | 6/2014 | Seeney ............ A61M 15/0021 128/203.15 |
| 2016/0039955 | A1 | 2/2016 | Klein et al. |
| 2017/0049974 | A1 | 2/2017 | Wensley et al. |
| 2018/0214661 | A1 * | 8/2018 | Rowland ............... A61M 16/10 |

FOREIGN PATENT DOCUMENTS

| | | |
|---|---|---|
| JP | 2012531961 A | 12/2015 |
| WO | 2015080653 A1 | 6/2015 |
| WO | 2018/223109 A1 | 12/2018 |

* cited by examiner

INHALER AND METHODS OF USING AND MAKING THE SAME

CROSS-REFERENCE TO RELATED APPLICATIONS

This application is a U.S. National Phase of International Application No. PCT/US2018/022732 filed Mar. 15, 2018, which claims priority to U.S. Provisional Patent Application Nos. 62/471,661, filed Mar. 15, 2017, and 62/514,072, filed Jun. 2, 2017, which are incorporated herein by reference in their entireties.

CROSS-REFERENCE TO RELATED APPLICATION

The present application claims priority to U.S. Provisional Patent Application No. 62/471,661, titled "METHODS AND DEVICES FOR FACILITATING DESIRABLE POWDERED DOSE RING POCKET CAVITY AIR FLOW" and filed Mar. 15, 2017, and U.S. Provisional Patent Application No. 62/514,072, titled "METHODS AND DEVICES FOR FACILITATING DESIRABLE POWDERED DOSE RING POCKET CAVITY AIR FLOW" and filed Jun. 2, 2017, which are both herein incorporated by reference.

FIELD

This presently disclosed technology relates generally to inhalers. More particularly, in one embodiment, the presently disclosed technology relates to methods and devices for facilitating inhalation of dry powder medicament.

BACKGROUND AND DESCRIPTION OF RELATED ART

Dry powder inhalers, or "DPIs," of the prior art provide multiple doses of a powdered drug product to a patient, which a patient self-administers through respiration. U.S. Patent Application Publication No. 2014/0007875, which is incorporated herein by reference, describes one prior art DPI, which includes discs having capsules containing dry powder and an apparatus that facilitates dispensing a dose of the powder from one capsule at a time upon inhalation by a user. U.S. Patent Application Publication No. 2009/0084379, which is also incorporated herein by reference, discloses a DPI with a single air flow path to facilitate administration of the dry powder.

Although prior art DPIs are useful and can be beneficial, at least one issue with prior art DPIs, particularly those that contain many doses, is that the small volume of each individual powder-containing pocket can make it difficult for such DPIs to function due to insufficient air flow. At least certain prior art dose ring geometry, when filled with the powder and then ultrasonically welded with an aluminum foil disc, may provide insufficient venturi air flow pattern to allow the pre-cut via laser aluminum foil to lift, to allow the powder to dispense. Each pocket in at least certain prior art designs has only a single opening (i.e., covered by the foil) and an otherwise solid interior wall geometry that does not allow any permeation of air. The powder is only lifted due to a pressure differential of the air above the aluminum foil (and the single opening) being greater than the pressure differential inside the headspace of the cavity.

In previous designs, there is often insufficient pressure differential or air flow to allow the aluminum foil flap to lift and the powder to be dispensed. In addition, necessary sealing means to preserve the product may be configured to impede proper functioning at the time of use if air flow is insufficient.

SUMMARY

There is a need in the art to address the above and other issues of prior art DPIs. The presently disclosed technology achieves the above and other objectives.

In one embodiment, at least one issue of prior art designs is solved by providing an additional air flow path via an airflow entry point (e.g., a second opening) into each pocket cavity. By incorporating an airflow entry point into or adjacent each pocket, when the user inhales into the air duct, the venturi air flow pattern velocity across the top of the pre-cut aluminum foil flap, combined with the airflow entry point in or adjacent each pocket, provides sufficient air flow volume to allow the aluminum foil flap to lift. This lifting of the aluminum foil flap, in turn, allows the powder to dispense from the pocket cavity and into the air duct, ultimately into the patient's mouth, thereby administering a metered dose of medicament.

One aspect of the presently disclosed technology includes a dose ring for a dry powder inhaler, which includes an annular aluminum foil member covering particulate medication cavities and through holes in a first portion of an annular member, and a second portion of the annular member having cutouts corresponding to the particulate medication cavities in the first portion of the annular member. The foil member can include hinged flaps formed by a C-shaped cut, so that one radial side is uncut and forms a hinge. Each hinged flap can cover both a cavity in the first portion of the annular member for particulate medication and a through hole located between that cavity and a circular inside edge of the second portion of the annular member.

In another aspect, the presently disclosed technology includes a plastic air duct for a DPI. The air duct can form an airflow channel configured to direct air through a hole in a dose ring to open a hinged flap, which can be configured to cover both the hole and a cavity containing particulate medication. The air can then be directed over the then-uncovered cavity to carry the particulate medication by the venturi effect through the DPI into the mouth of the user.

In yet another aspect, the presently disclosed technology is directed to an inhaler for facilitating administration of dry powder. The inhaler includes a body defining an interior space and includes a mouth piece. The inhaler includes at least one member within the interior space of the body. The at least one member includes at least one compartment, at least one flap, and at least one conduit. The at least one compartment defines a cavity configured to hold dry powder and includes an opening configured to release the dry powder when the at least one flap is moved from a closed position to an open position. The at least one flap covers at least a portion of one end of the at least one conduit when the flap is in the closed position.

In still another aspect, the presently disclosed technology is directed to inhaling or evacuating air from within the interior space of the body through the mouth piece, thereby causing air to move through the at least one conduit and lift the flap.

BRIEF DESCRIPTION OF SEVERAL VIEWS OF THE DRAWINGS

The foregoing summary, as well as the following detailed description of the presently disclosed technology, will be better understood when read in conjunction with the appended drawings, wherein like numerals designate like elements throughout. For the purpose of illustrating the presently disclosed technology, there are shown in the drawings various illustrative embodiments. It should be understood, however, that the presently disclosed technology is not limited to the precise arrangements and instrumentalities shown. In the drawings.

DETAILED DESCRIPTION

While systems, devices and methods are described herein by way of examples and embodiments, those skilled in the art recognize that the presently disclosed technology is not limited to the embodiments or drawings described. Rather, the presently disclosed technology covers all modifications, equivalents and alternatives falling within the spirit and scope of the appended claims. Features of any one embodiment disclosed herein can be omitted or incorporated into another embodiment.

Any headings used herein are for organizational purposes only and are not meant to limit the scope of the description or the claims. As used herein, the word "may" is used in a permissive sense (i.e., meaning having the potential to) rather than the mandatory sense (i.e., meaning must). Unless specifically set forth herein, the terms "a," "an" and "the" are not limited to one element but instead should be read as meaning "at least one." The terminology includes the words noted above, derivatives thereof and words of similar import.

According to an aspect of the presently disclosed technology, the aforementioned problems with previous designs are solved by providing an additional air flow path via an airflow entry point into or adjacent each pocket cavity. By incorporating an airflow entry point into or adjacent each pocket, when the user inhales into the air duct, the venturi air flow pattern velocity across the top of the pre-cut aluminum foil flap, combined with the airflow entry point in or adjacent each pocket, will provide sufficient air flow volume to allow the aluminum foil flap to lift. This lifting of the aluminum foil flap, in turn, allows the powder with active product ingredient (API) to dispense from the pocket cavity and into the air duct, ultimately into the patient's mouth, thereby administering a metered dose of powdered API.

Referring now in detail to the various figures, wherein like reference numerals refer to like parts throughout, FIGS. 1-9 illustrate one embodiment of a device or inhaler, generally designated 10, for facilitating inhalation of powder, such as dry powder medicament 44 or powder with API (see FIGS. 7-9). The inhaler 10 can include a body 25 having an end cap 23 at one end thereof and a mouthpiece 26 at an opposing end thereof. End cap 23 can include or be formed of an active material 24 (e.g., desiccant), as described in detail below. The body 25 defines or surrounds an interior space, and the mouthpiece 26 can define a pathway that is fluidly connected to the interior space of the body 25. The mouthpiece 26 allows a user to draw or inhale air containing the powder.

A cover 28 can be removably and/or pivotally attached to the body 25. In one embodiment, the cover 28 is attached via a hinge to the body 25. The cover 28 can be movable with respect to the body 25 between a closed position (see FIG. 1) and an open position. When the cover 28 is in the closed position, the mouthpiece 26 is covered and/or protected. When the cover 28 is in the open position, the mouthpiece 26 is exposed and able to be engaged or contacted by the user. The cover 28 can include a pivotable trigger 27, as described in more detail below.

One or more of the body 25, the end cap 23 and the cover 28 can be formed of a low moisture vapor transfer rate (LMVT) plastic. The LMVT material reduces moisture ingress during storage and use of the device 10. When closed and/or fully attached (see FIG. 1), the combined body 25, end cap 23 and cover 28 form a tightly sealed DPI. By designing a tightly sealed DPI device and using desiccant plastic for controlling moisture within it, improved powder dispersion and reduced capillary forces can be expected as compared to the prior art.

In one embodiment, the inhaler 10 includes only nine parts, eight of which are injection molded. This design removes the need for piercing the material securing the powder prior to dispersing the powder, which is required by some prior art designs. The design of the presently disclosed technology also eliminates the risk of contaminating the drug formulation with debris from a piercing mechanism.

Figure 1:
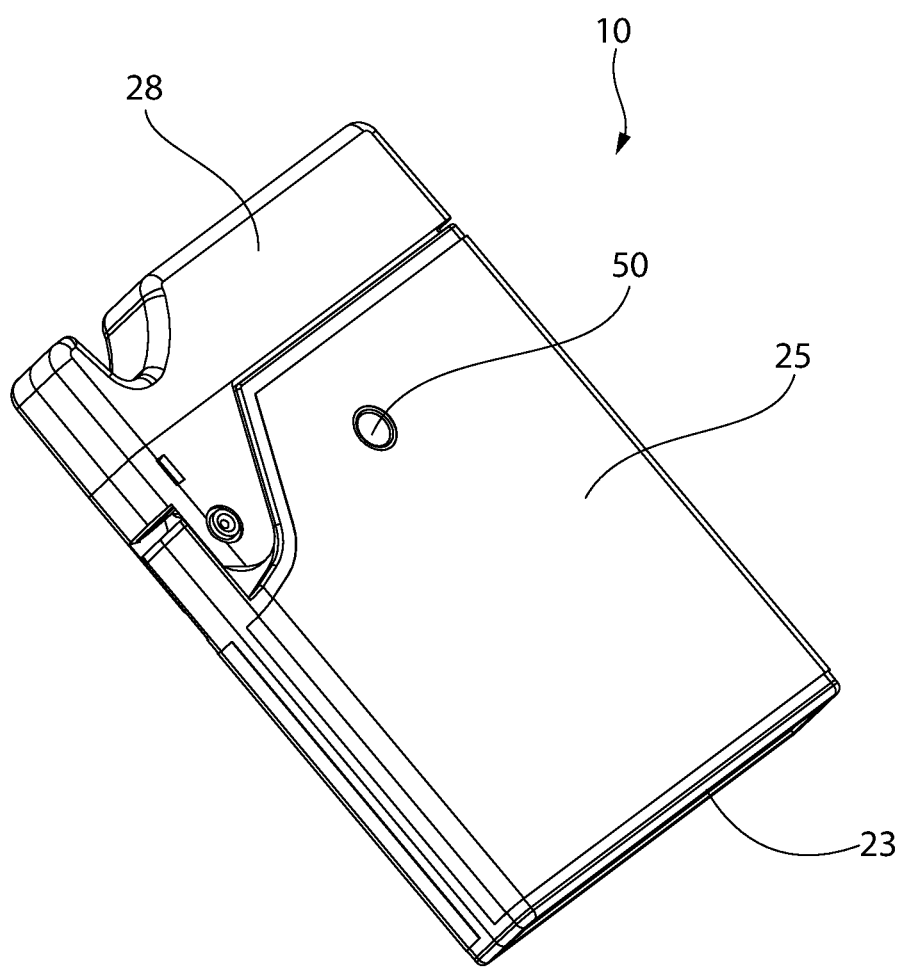
FIG. 1 is a perspective view of an inhaler according to an embodiment of the present disclosed technology, wherein the inhaler is shown from a first side.
Figure 2:
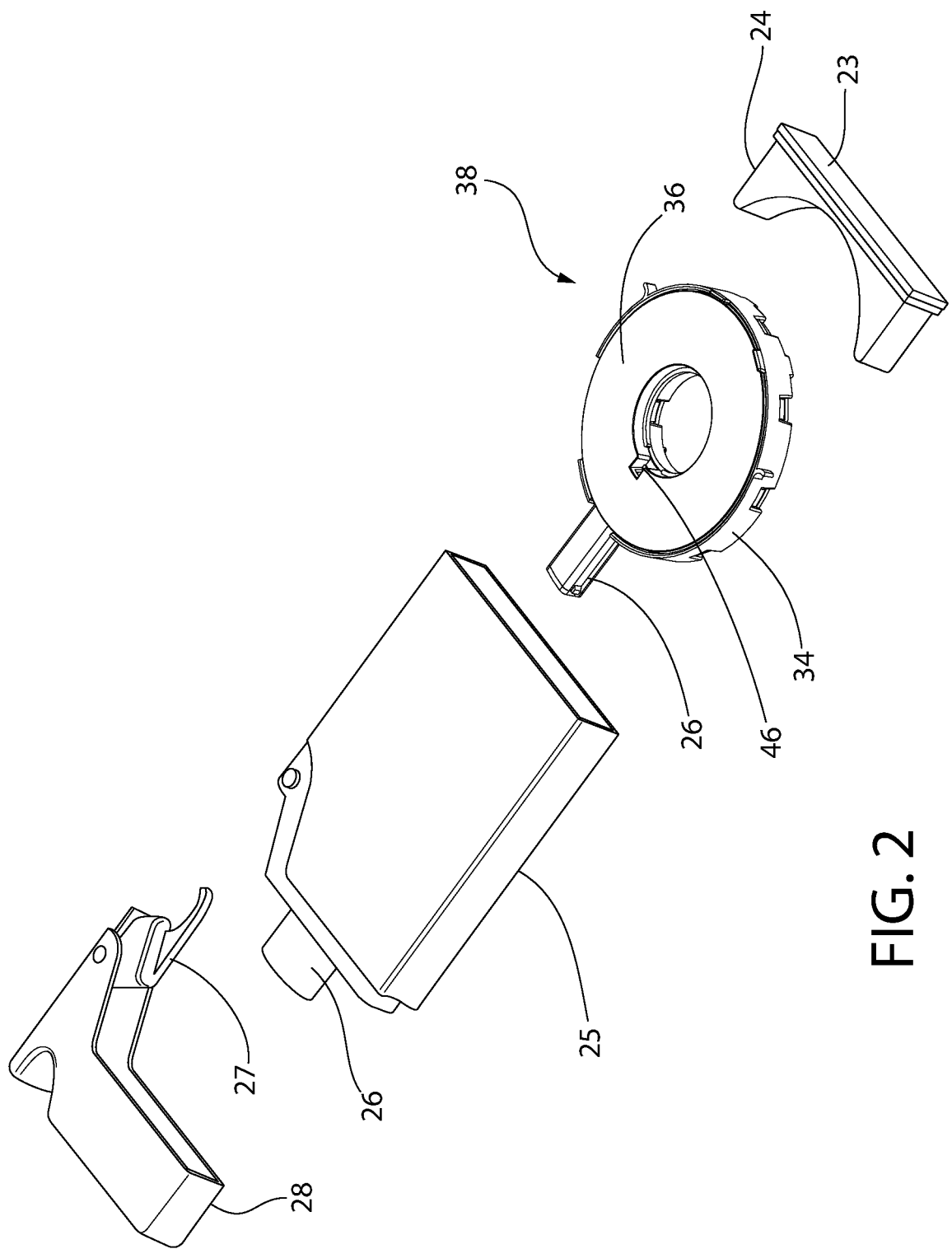
FIG. 2 is a partially exploded perspective view of the inhaler, wherein the inhaler is shown from an opposite second side.
Figure 3:
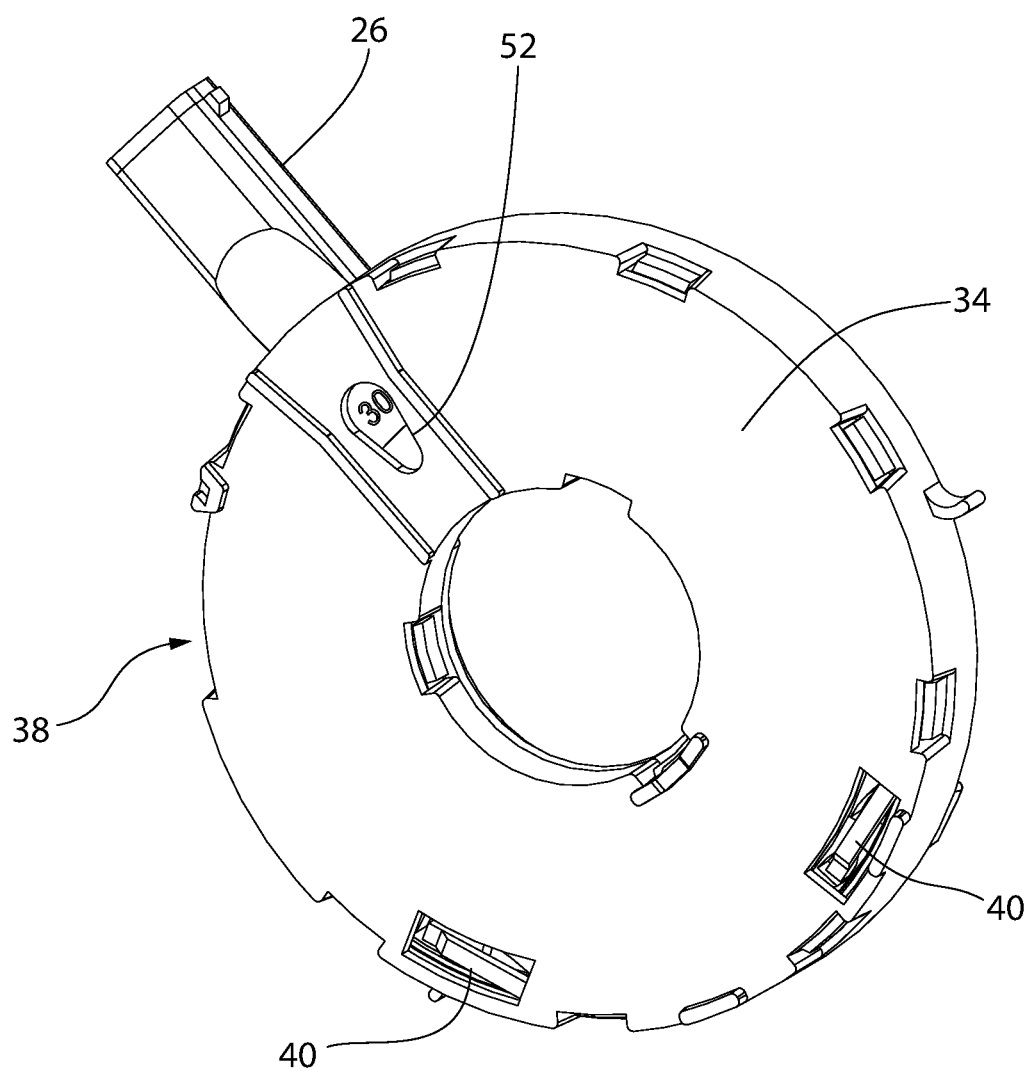
FIG. 3 is a perspective view of at least some interior components of the inhaler shown in FIG. 2, wherein the components are shown from the first side shown in FIG. 1.
Figure 4:
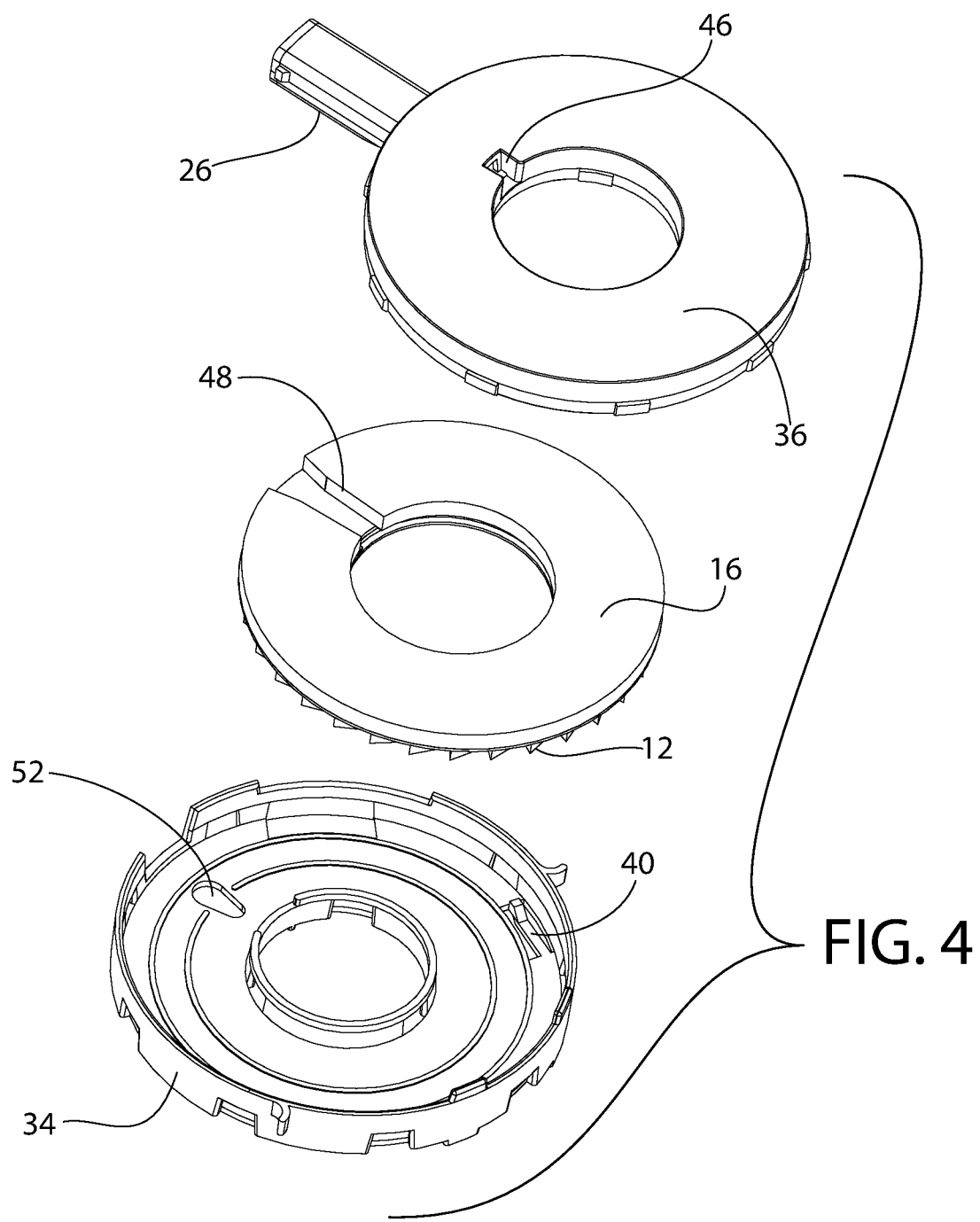
FIG. 4 is a partially exploded perspective view of the interior components shown in FIG. 2.
Figure 5:
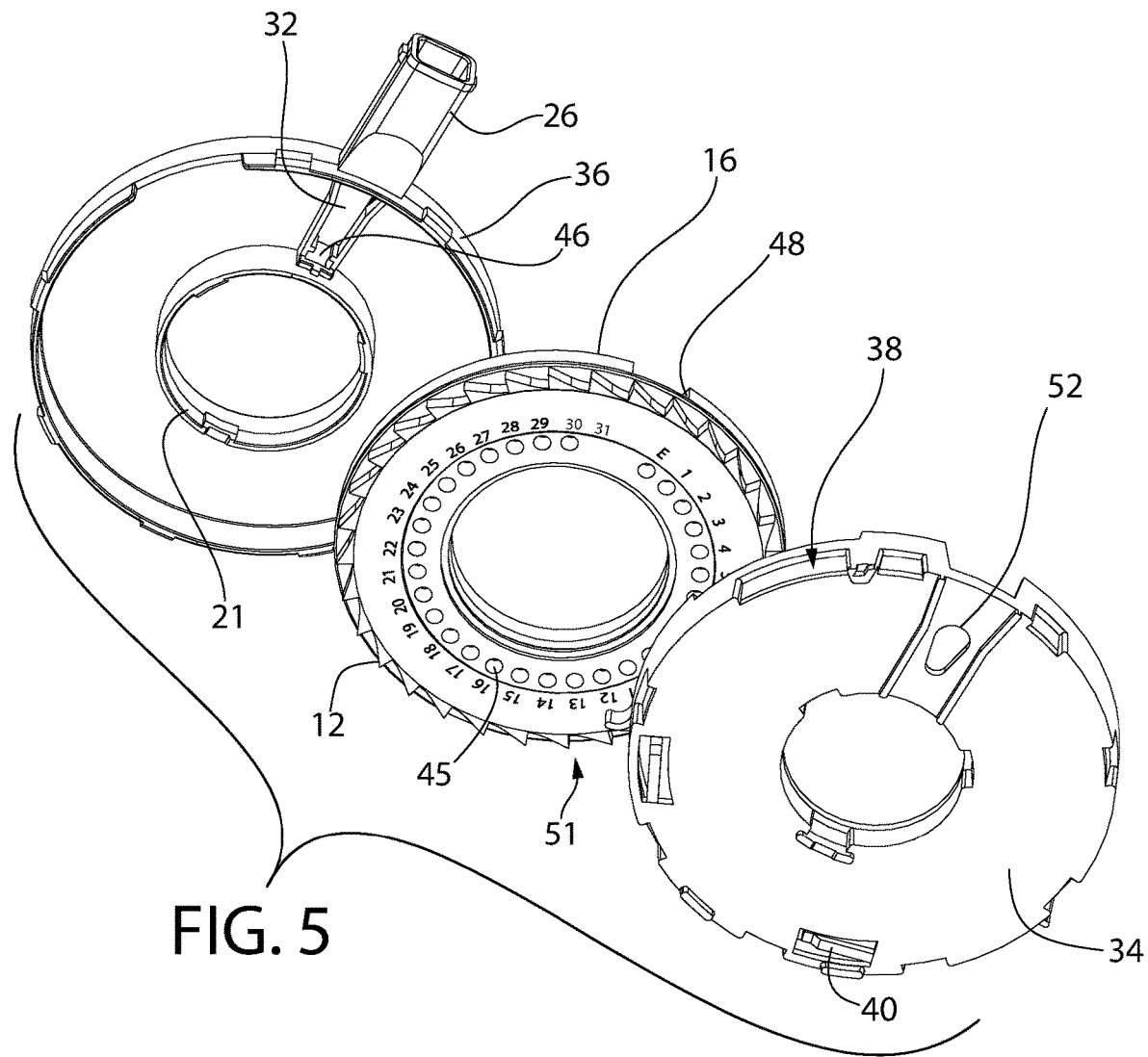
FIG. 5 is another partially exploded perspective view of the interior components shown in FIG. 4, wherein the components are shown from the first side shown in FIG. 1.
Figure 6:
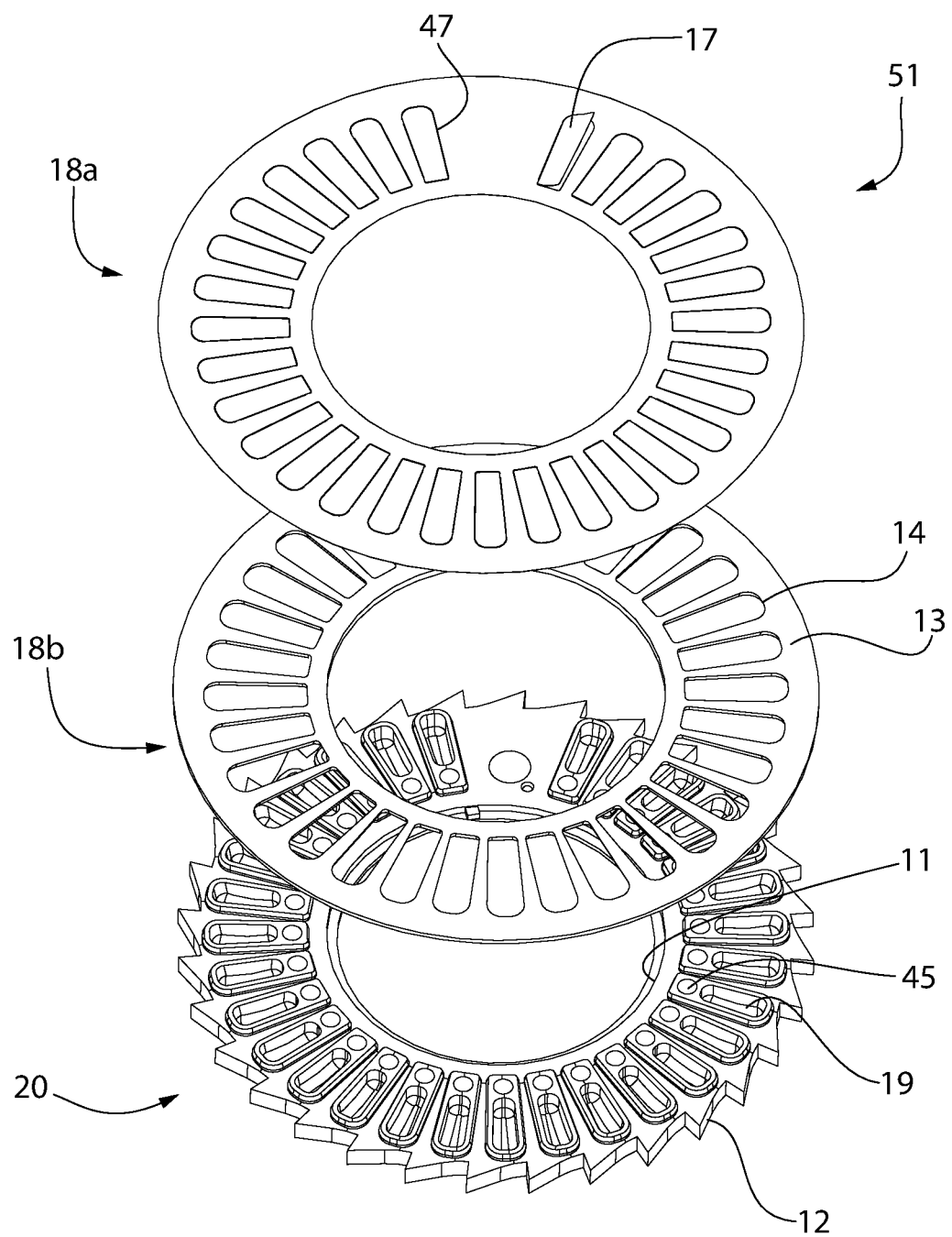
FIG. 6 is a perspective view of an annular member visible in FIGS. 4 and 5.

The inhaler 10 includes at least one member 51 positioned within the interior space of the body 25. In one embodiment, as shown in FIGS. 4-6, the at least one member 51 is an annular member or a dose ring that is rotatable with respect to the body 25. In another embodiment, the member 51 can be a linear member or a dose line. The member 51 can be configured to provide a plurality of separate doses of medicament. In yet another embodiment, the member 51 can be configured to provide only a single dose of medicament.

As shown in FIGS. 2-5, one embodiment of the annular member 51 can be supported or enclosed within the body 25 by a first tray 34 and a second tray 36. Both the first tray 34 and the second tray 36 can have a generally circular outer periphery and a generally circular inner periphery. In one embodiment, at least a portion of the second tray 36 can fit within the first tray 34. An air duct 32 (see FIG. 5) can be arranged or formed within the second tray 36 and can connect an opening 46 through a top and/or side wall of the second tray 36 to the passageway of the mouth piece 26. In one embodiment, the mouth piece 26 is an integral or unitary portion of the second tray 36.

As shown in FIG. 5, the second tray 36 can include a circular center guide 21. The annular member 51 can fit or be positioned within or between the first tray 34 and the second tray 36, and the annular member 51 can rotate with respect to both the first tray 34 and the second tray 36. More particularly, in one embodiment, the annular member 51 is placed around the center guide 21 when placed in the second tray 36. A spacer 16, optionally formed of foam, can be positioned between the annular member 51 and an interior surface of the second tray 36. The spacer 16 can include an opening or cut-out 48. The spacer 16 can be arranged in the second tray 36 so that the spacer 16 is positioned on both sides of the air duct 32.

Optionally, the first tray 34 (and/or the second tray 36) can include at least one stop or spring 40 extending at least partially into an interior of the first tray 34 in a biased or relaxed state. In another embodiment, the first tray 34 can include two or more spaced-apart springs 40. Each spring 40 can inhibit rotation of the annular member 51 with respect to the first tray 34 and the second tray 36. In one embodiment, each spring 40 is a leaf spring with one end thereof integrally or unitarily formed with a base wall of the first tray 34. An interior surface of each spring 40 can include a projection or an angled surface.

Referring to FIG. 6, in one embodiment, the annular member 51 is formed of three parts or components: a first annular member 18a, a second annular member 18b, and a third annular member 20. In one embodiment, the first annular member 18a is formed of aluminum foil. Optionally, the first annular member 18a includes cuts that form a plurality of spaced-apart and generally identical hinged flaps 17. In FIG. 6, the one flap 17 identified with a reference number is shown in a partially open position, and the remaining flaps 17 are shown closed. In one embodiment, the cuts can be formed in the shape of a "C," and a hinge 47 is created by an uncut edge of each flap 17. Optionally, the first annular member 18a includes at least thirty separate flaps 17. The flaps 17 can be equidistantly spaced around the first annular member 18a, except that a blank or solid space is formed between two particular flaps 17. In one embodiment, a width of the blank space is approximately twice the width of a single flap 17.

Optionally, the first annular member 18a is bonded to an upper surface 13 (or lower surface, depending upon orientation of the device 10) of the second annular member 18b. In another embodiment, the first annular member 18a is integrally and unitarily formed with the second annular member 18b, such that the annular member 51 is only formed of two parts or components. The second annular member 18b can include a plurality of spaced-apart holes 14, each of which are aligned with one of the cuts of the first annular member 18a so as to define a passageway through the second annular member 18b when the flaps 17 are opened. The holes 14 of the second annular member 18b can be generally oval-shaped.

The third annular member 20 can include or define a plurality of spaced-apart compartments, capsules or dose pocket cavities 19. Each compartment 19 can be sized, shaped, and/or configured to hold a predetermined amount of powder, such as a daily dose of a powder medicament. Optionally, each compartment 19 can be sized to contain or hold 10-13 mg of powder 44. Each compartment 19 includes at least one opening so as to allow the powder 44 to be inserted into the compartment 19 and removed from the compartment 19 at the desired time. Each flap 17 covers the opening of the respective compartment 19, includes an extension extending beyond an outer edge of the opening when the flap 17 is in the closed position. At least a portion of an underside of the extension of each flap 17 is free or unattached to any structure.

One continuous or a plurality of spaced-apart conduits can be positioned proximate the compartments 19, such as radially inwardly of each compartment 19. At least a portion of the underside of each flap 17 faces the associated or respective conduit(s). In one embodiment, each of the plurality of spaced-apart conduits is a hole 45 through the third annular member 20. Each hole 45 can correspond to or be positioned next to, but spaced-apart from, one of the compartments 19. In one embodiment, the opening that defines the hole 45 in the third annular member 20 is smaller than the opening of the respective compartment 19. Optionally, each hole 45 can be located next to the respective compartment 19 toward an inside edge 11 of third annular member 20. In one embodiment, each hole 45 extends through the third annular member 20, while each compartment 19 does not extend through the third annular member 20 so as to hold the medicament. In an alternative embodiment, the plurality of spaced-apart holes 45 can be replaced by a single, continuous channel or conduit that extends around and through the third annular member 20. The channel can function the same as the plurality of spaced-apart holes 45 described above.

When combined, the first, second and third annular members 18a, 18b, 20 seal the powder within the dose cavity 19 unless and until the flap 17 is opened. In one embodiment, although the cut allows each flap 17 to be opened more easily, the cut does not destroy the sealing capacity of the combined first, second and third annular members 18a, 18b, 20. In one embodiment, the first annular member 18a is formed of a thin layer of aluminum foil that is in-mold labeled to the second annular member 18b and then ultrasonically welded to the third annular member 18. Optionally, the second annular member 18b and the third annular member 20 can be molded plastic, such as medical-grade plastic.

In one alternative embodiment, instead of each flap 17 being associated with one of the compartments 19, as described in detail above, each flap 17 can cover and/or be associated with two or more separate and spaced-apart compartments 19. Each of these compartments 19 can contain the same type or kind of powder 44. In an alternative embodiment, at least two adjacent compartments 19 associated with one of the flaps 17 can contain different types or kinds of powder or medicament 44 that cannot or should not be mixed during storage, but can and/or should be delivered simultaneously or substantially simultaneously when inhaled by the user.

A plurality of spaced-apart ridges or teeth 12 can extend around the outer periphery of the third annular member 20. The teeth 12 can extend evenly or equidistantly spaced-apart around the entire periphery of the third annular member 20. At least a portion of the trigger 27 can contact or engage one of the teeth 12 of the annular member 51 through an opening 38 formed in a sidewall of the housing 25. The trigger 27 can be spring-loaded. Alternatively, the trigger 27 can omit the spring and simply move or rotate the annular member 51 upon opening the cover 28, such as shown in FIGS. 4A-4C of U.S. Application Publication No. 2014/0007875. Selective engagement of the trigger 27 with teeth 12 of the annular member 51 can overcome the force of each spring 40 on the annular member 51 to rotate or "advance" the annular member 51 within the combined first tray 34 and the second tray 36. Each spring 40 can provide a tactical and/or audible action in response to the trigger 27 overcoming the biasing force of each spring 40.

Referring specifically to FIGS. 1 and 3-5, the housing 25 can include a window 50 in one of the walls thereof. The first tray 34 can include an opening 52 through a base wall thereof. The opening 52 of the first tray 34 can be aligned with the window 50 when the first tray 34 is properly positioned within the housing 25. The third annular member 20 can include a plurality of spaced-apart indicia, such as chronological or consecutive numerals and/or letters (e.g., 30, 29, 28, 27, etc.). Each one of the indicia can be located proximate to one of the compartments 19, but on an opposite side from where the compartments 19 are formed.

In one embodiment, the active material 24 is a desiccant. This would be an embodiment where moisture absorption is desired. However, where moisture absorption is not desired, the active material 24 can include alternative active agents. For example, in another embodiment, the active material 24 contains a material selected from the group consisting of activated carbon, carbon black, ketcham black and diamond powder. In a further embodiment, an active agent including one or more layers of the active material 24 contains a material such as absorption microspheres, $BaTiO_3$, $SrTiO_3$, $SiO_2$, $Al_2O_3$, $ZnO$, $TiO_2$, $MnO$, $CuO$, $Sb_2O_3$, silica, calcium oxide and ion exchange resins. In yet another embodiment, an absorbing agent containing layer of the active material 24 contains two or more types of absorbing agents. The suitable absorbing agent is chosen so as to achieve absorption of the desired vapor or gas for the desired end use (e.g. absorption of moisture, oxygen, carbon dioxide, nitrogen or other undesired gases or vapors).

The active material 24 (whether desiccant, oxygen scavenger, a releasing material or agent, etc., or combination thereof) is capable of acting on, interacting with or reacting with a selected material (e.g., moisture or oxygen). Examples of such actions or interactions may include absorption, adsorption (sorption, generally) or release of the selected material.

The active material 24 can include an "active agent" in a base material. The active agent (i) can be immiscible with the base material (e.g., polymer) and when mixed and heated with the base polymer and a channeling agent, will not melt, i.e., has a melting point that is higher than the melting point for either the base polymer or the channeling agent, and/or (ii) acts on, interacts or reacts with a selected material. The term "active agent" may include but is not limited to materials that absorb, adsorb or release the selected material(s). Active agents according to the presently disclosed technology may be in the form of particles such as minerals (e.g., molecular sieve or silica gel, in the case of desiccants), but the presently disclosed technology should not be viewed as limited only to particulate active agents. For example, in some embodiments, an oxygen scavenging formulation may be made from a resin which acts as, or as a component of, the active agent.

As used herein, the term "base material" is a component (preferably a polymer) of an entrained active material, other than the active agent, that provides structure for the entrained material.

As used herein, the term "base polymer" is a polymer optionally having a gas transmission rate of a selected material that is substantially lower than, lower than or substantially equivalent to, that of the channeling agent. By way of example, such a transmission rate would be a water vapor transmission rate in embodiments where the selected material is moisture and the active agent is a water absorbing desiccant. The primary function of the base polymer is to provide structure for the entrained polymer. Suitable base polymers may include thermoplastic polymers, e.g., polyolefins such as polypropylene and polyethylene, polyisoprene, polybutadiene, polybutene, polysiloxane, polycarbonates, polyamides, ethylene-vinyl acetate copolymers, ethylene-methacrylate copolymer, poly(vinyl chloride), polystyrene, polyesters, polyanhydrides, polyacrylianitrile, polysulfones, polyacrylic ester, acrylic, polyurethane and polyacetal, or copolymers or mixtures thereof.

Referring to such a comparison of the base polymer and channeling agent water vapor transmission rate, in one embodiment, the channeling agent has a water vapor transmission rate of at least two times that of the base polymer. In another embodiment, the channeling agent has a water vapor transmission rate of at least five times that of the base polymer. In another embodiment, the channeling agent has a water vapor transmission rate of at least ten times that of the base polymer. In still another embodiment, the channeling agent has a water vapor transmission rate of at least twenty times that of the base polymer. In still another embodiment, the channeling agent has a water vapor transmission rate of at least fifty times that of the base polymer. In still another embodiment, the channeling agent has a water vapor transmission rate of at least one hundred times that of the base polymer.

As used herein, the term "channeling agent" or "channeling agents" is defined as a material that is immiscible with the base polymer and has an affinity to transport a gas phase substance at a faster rate than the base polymer. Optionally, a channeling agent is capable of forming channels through the entrained polymer when formed by mixing the channeling agent with the base polymer. Optionally, such channels are capable of transmitting a selected material through the entrained polymer at a faster rate than in solely the base polymer.

As used herein, the term "channels" or "interconnecting channels" is defined as passages formed of the channeling agent that penetrate through the base polymer and may be interconnected with each other.

As used herein, the term "entrained polymer" is defined as a monolithic material formed of at least a base polymer with an active agent and optionally also a channeling agent entrained or distributed throughout. An entrained polymer thus includes two-phase polymers and three-phase polymers. A "mineral loaded polymer" is a type of entrained polymer, wherein the active agent is in the form of minerals, e.g., mineral particles such as molecular sieve or silica gel. The term "entrained material" is used herein to connote a monolithic material comprising an active agent entrained in a base material wherein the base material may or may not be polymeric.

As used herein, the term "monolithic," "monolithic structure" or "monolithic composition" is defined as a composition or material that does not consist of two or more discrete macroscopic layers or portions. Accordingly, a "monolithic composition" does not include a multi-layer composite.

As used herein, the term "phase" is defined as a portion or component of a monolithic structure or composition that is uniformly distributed throughout, to give the structure or composition it's monolithic characteristics.

As used herein, the term "selected material" is defined as a material that is acted upon, by, or interacts or reacts with an active agent and is capable of being transmitted through the channels of an entrained polymer. For example, in embodiments in which a desiccant is used as an active agent, the selected material may be moisture or a gas that can be absorbed by the desiccant. In embodiments in which a releasing material is used as an active agent, the selected material may be an agent released by the releasing material, such as moisture, fragrance, or an antimicrobial agent (e.g., chlorine dioxide). In embodiments in which an adsorbing material is used as an active agent, the selected material may be certain volatile organic compounds and the adsorbing material may be activated carbon.

As used herein, the term "three phase" is defined as a monolithic composition or structure comprising three or more phases. An example of a three phase composition according to the presently disclosed technology would be an entrained polymer formed of a base polymer, active agent, and channeling agent. Optionally, a three phase composition or structure may include an additional phase, e.g., a colorant.

Entrained polymers may be two phase formulations (i.e., comprising a base polymer and active agent, without a channeling agent) or three phase formulations (i.e., comprising a base polymer, active agent and channeling agent). Entrained polymers are described, for example, in U.S. Pat. Nos. 5,911,937, 6,080,350, 6,124,006, 6,130,263, 6,194,079, 6,214,255, 6,486,231, 7,005,459, and U.S. Pat. Pub. No. 2016/0039955, each of which is incorporated herein by reference in its entirety.

An entrained material or polymer includes a base material (e.g., polymer) for providing structure, optionally a channeling agent and an active agent. The channeling agent forms microscopic interconnecting channels through the entrained polymer. At least some of the active agent is contained within these channels, such that the channels communicate between the active agent and the exterior of the entrained polymer via microscopic channel openings formed at outer surfaces of the entrained polymer. The active agent can be, for example, any one of a variety of absorbing, adsorbing or releasing materials, as described in further detail below. While a channeling agent is preferred, the invention broadly includes entrained materials that optionally do not include channeling agents, e.g., two phase polymers.

In any embodiment, suitable channeling agents may include a polyglycol such as polyethylene glycol (PEG), ethylene-vinyl alcohol (EVOH), polyvinyl alcohol (PVOH), glycerin polyamine, polyurethane and polycarboxylic acid including polyacrylic acid or polymethacrylic acid. Alternatively, the channeling agent can be, for example, a water insoluble polymer, such as a propylene oxide polymerisate-monobutyl ether, such as Polyglykol B01/240, produced by CLARIANT. In other embodiments, the channeling agent could be a propylene oxide polymerisate monobutyl ether, such as Polyglykol B01/20, produced by CLARIANT, propylene oxide polymerisate, such as Polyglykol D01/240, produced by CLARIANT, ethylene vinyl acetate, nylon 6, nylon 66, or any combination of the foregoing.

Suitable active agents according to the presently disclosed technology include absorbing materials, such as desiccating compounds. If the active agent is a desiccant, any suitable desiccant for a given application may be used. Typically, physical absorption desiccants are preferred for many applications. These may include molecular sieves, silica gels, clays and starches. Alternatively, the desiccant may be a chemical compound that forms crystals containing water or compounds which react with water to form new compounds.

Optionally, in any embodiment, the active agent may be an oxygen scavenger, e.g., an oxygen scavenging resin formulation.

Table 1 below shows the characterization of the designed desiccant moisture adsorption capacity and the consumption of the capacity due to moisture ingress into the device following exposure to calculated moisture amounts at various stages of manufacturing, storage, and use of the DPI device of one embodiment of the presently disclosed technology.

TABLE 1

Moisture ingress and consumption of desiccant moisture adsorption capacity.

| | Stage Desiccant Plastic Part/DPI Device | | | | | | |
|---|---|---|---|---|---|---|---|
| | Design | Molding | Storage | Assembly | Shelf-Life | Use-Life | 30 Uses | Remaining |
| Moisture Ingress, mg | N/A | 6 | 160 | 8 | 130 | 306 | 10 | N/A |
| Desiccant Moisture Adsorption Capacity, mg | 750 | 744 | 584 | 576 | 446 | 140 | 130 | 130 |

The following are assumptions used for calculating the moisture ingress during the various stages of manufacturing the device described in Table 1 above:

Adsorption: 3,000 µg of water vapor is adsorbed in the molded desiccant part in 1 hour. In addition, 0.3 mg of latent moisture in molded plastic parts and PE Seal need to be adsorbed following device assembly.

Molding: molded desiccant plastic parts are exposed for at least 1 or 2 hours during molding before being placed in a foil bag that is sealed. (25° C./60% Relative Humidity (RH) Conditions).

Storage at molding facility: molded desiccant plastic parts are stored in sealed foil bags within a poly bag in shipping cartons. (25° C./60% RH Conditions).

Storage at Assembly Site: molded desiccant plastic parts are stored at Assembly Site for 1 year before parts are used for manufacturing devices. (25° C./60% RH Conditions)

Assembly: molded desiccant plastic parts are exposed for 2 hours during manufacturing as completed devices at Assembly Site and placed individually into a foil pouch that is sealed. Note: latent moisture in molded plastic parts and PE Seal are adsorbed following device assembly. (25° C./60% RH Conditions).

Shelf-Life: manufactured device is stored in a sealed foil pouch for 1 year before being opened for use. (30° C./75% RH Conditions).

Use-Life: device is stored closed during 60 days and available for use. (30° C./75% RH Conditions).

30 Uses: device is opened and re-closed 30 times over the 60 days of Use-Life. (30° C./75% RH Conditions).

Figure 7:
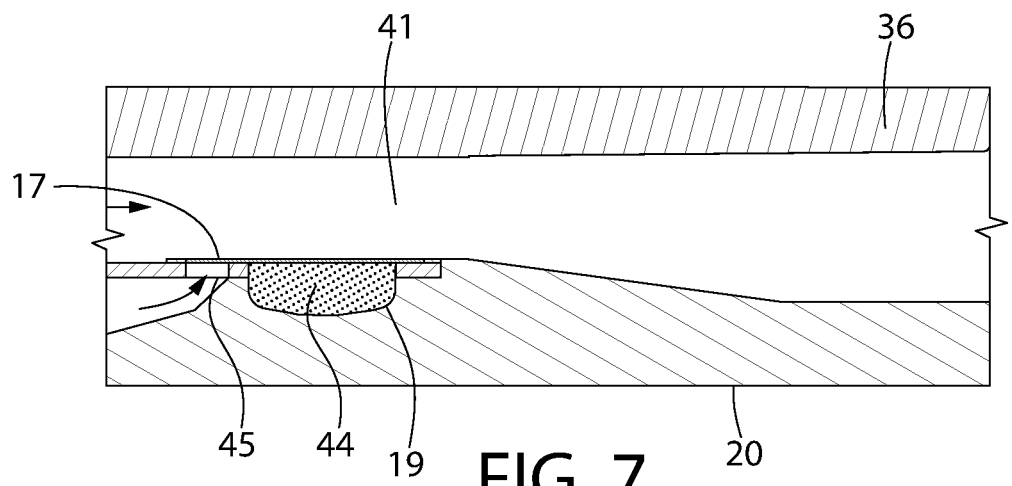
FIGS. 7-9 are sequential views of operation of lifting of a flap of the annular member and removal of powder toward a mouthpiece for inhalation by a user.
Figure 8:
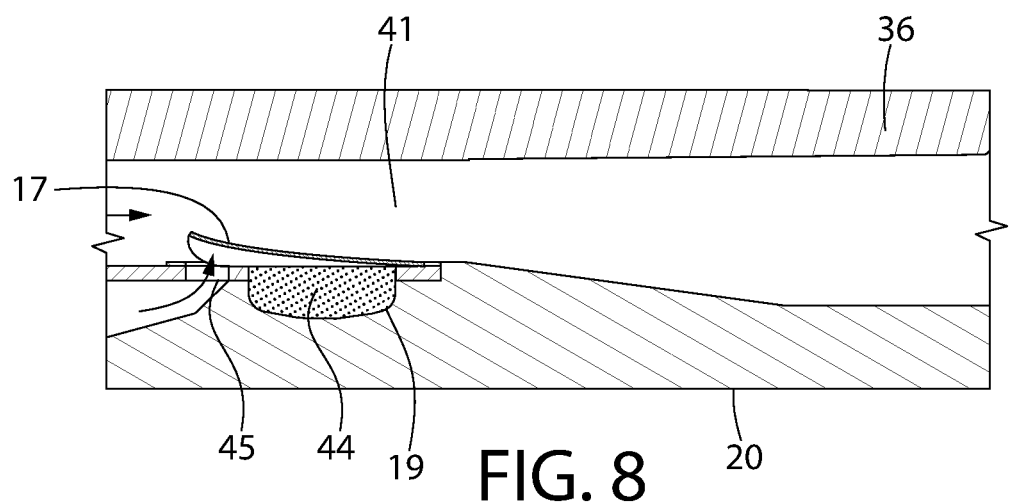
Figure 9:
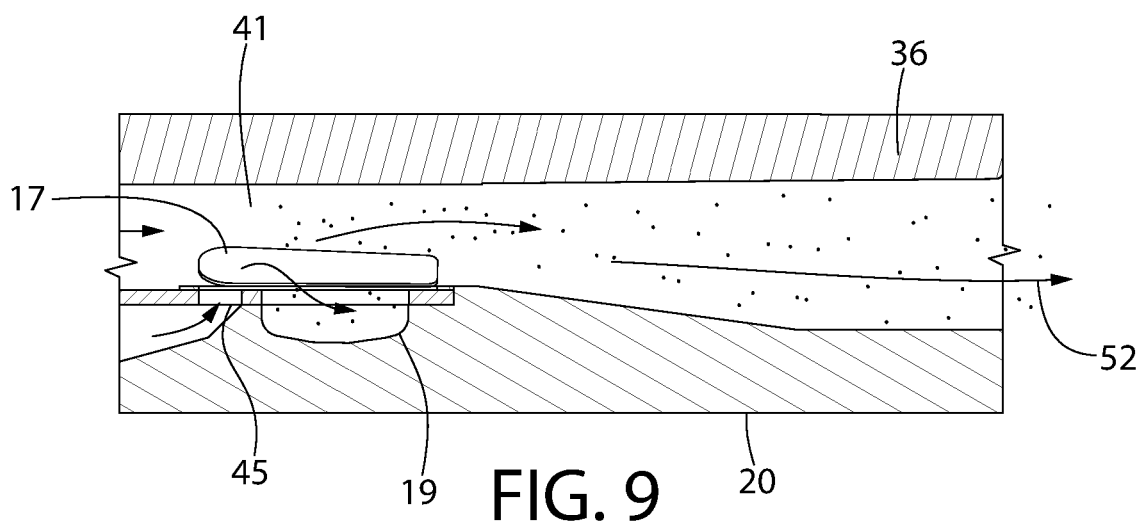

FIGS. 7-9 show operation of one embodiment of the device 10. For example, once the user engages the trigger 27 to rotate the annular member 51 to the desired position (e.g., when the correct day or dosage period is visible through the opening 52 of the first tray 34 and the window 50 of the housing 25, the user can inhale through the mouth piece 26. In one embodiment, this causes air to travel simultaneously through two separate paths, namely (i) from beneath and through the hole 45 that is positioned within the air duct 32 of the first tray 34 and (ii) through the opening 46 of the second tray 36 and then above the hole 45 and the compartment 19 within the air duct 32 of the first tray 34. In contrast to prior art designs, airflow in one embodiment of the presently disclosed technology is directed through one of the holes 45, which exerts pressure on a bottom surface of one of the flaps 17 to cause it to open. The size, shape and/or configuration of the air duct 32 can be modified or adjusted for different pathologies or different parts of the population (e.g., children or elderly).

The combination of air flow described above reliably and effectively moves the flap 17 aligned with or within the air duct 32 of the third tray 34 from the closed position to the opened position, thereby allowing the powder in the compartment 19 to be released or withdrawn by the venturi effect and travel to the user's mouth through the mouth piece 26. The spacer 16 is configured to maintain all of the flaps 17 not aligned with or within the air duct 32 of the third tray 34 in a closed position. Thus, the spacer 16 can maintain each the flaps 17 in a closed configuration, except where the opening 48 is aligned with the air duct 32. Any flap 17 positioned directly beneath or above the opening 48 can be opened upon a force exerted by the user. In certain embodiments, the spacer 16 can have a thickness of approximately 0.062 inches, 0.093 inches, or 0.125 inches, depending upon the force required to open the flaps 17 and/or the medicament used.

Figure 10:
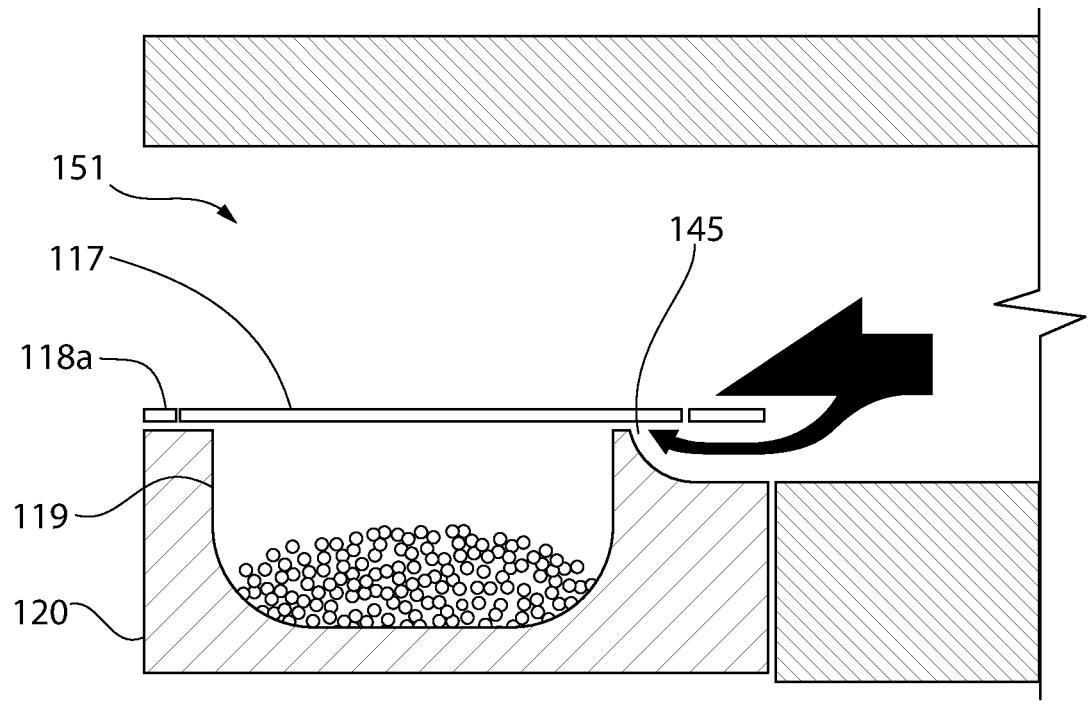
FIG. 10 is a cross-sectional side elevation view of a portion of an annular member according to an embodiment of the presently disclosed technology, wherein a flap of the annular member is shown in a closed position.
Figure 11:
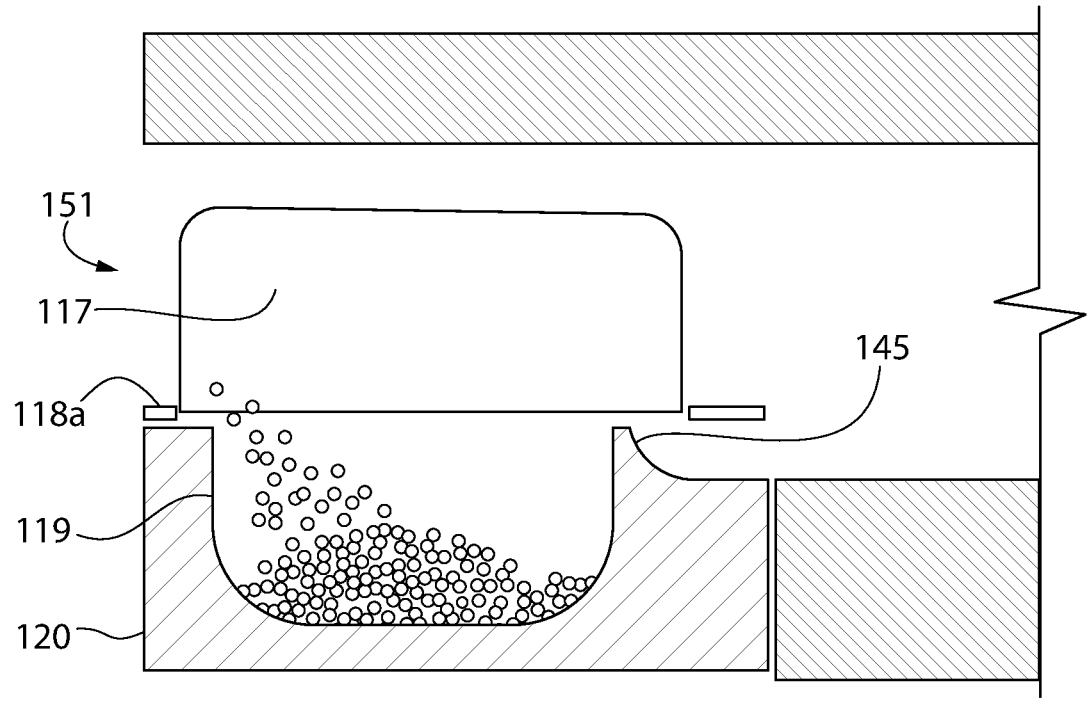
FIG. 11 is another cross-sectional side elevation view of the features shown in FIG. 10, wherein the flap is shown in an open position.
Figure 12:
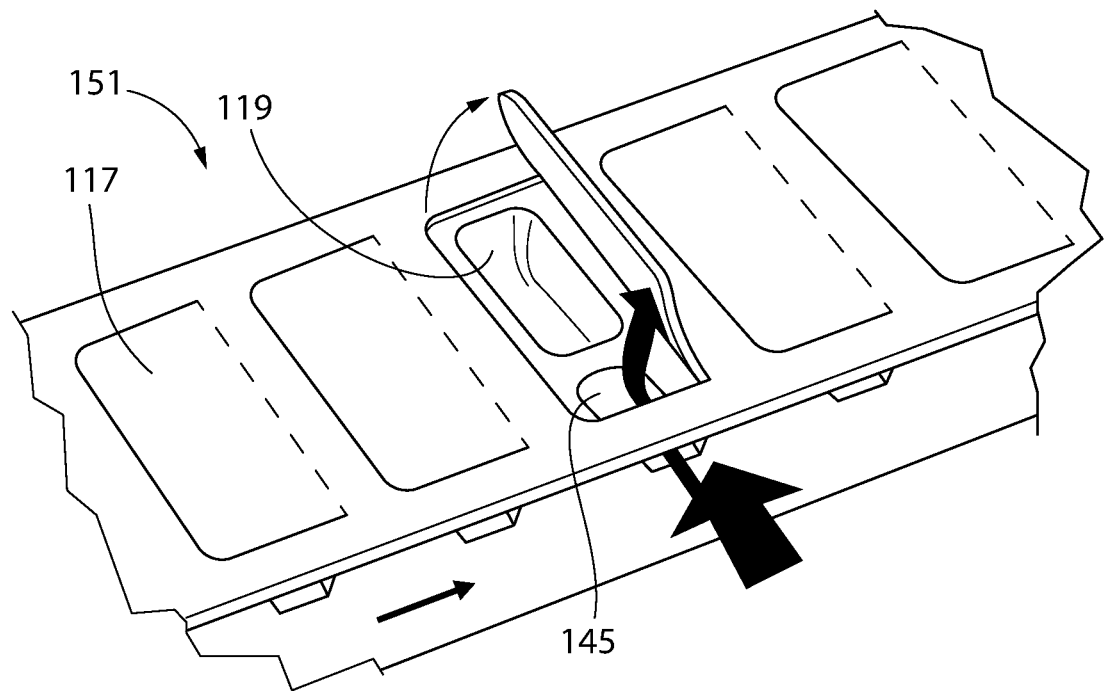
FIG. 12 is a perspective view of the features shown in FIG. 11.

FIGS. 10-12 show another embodiment of the presently disclosed technology. Similar or identical structure between the embodiments of FIGS. 1-9 and FIGS. 10-12 is distinguished in FIGS. 10-12 by a reference number with a magnitude one hundred (100) greater than that of FIGS. 1-9. Description of certain similarities between the embodiments may be omitted herein for convenience and brevity only.

In contrast to the previous embodiment, each flap 117 does not extend beyond the hole 145 around an entire periphery of the hole 145 when the flap 117 is in the closed position (see FIG. 10). Instead, an end of each flap 117 proximate the respective hole 145 has a bottom surface that is free or unsecured to any structure. In other words, an edge of each flap 117 can form a seal with a portion of an edge of the respective hole 145. This can reduce the force(s) needed to open each flap 117 and/or reduce the amount of material needed to form the first annular member 118a. As shown in FIG. 12, similar to the previous embodiment, each flap 117 extends beyond the compartment 119 around an entire perimeter of the compartment 119.

Referring to FIGS. 10 and 11, the present embodiment may omit the second annular member, such that the annular member 151 may only include two annular members 118a, 120, which are equivalent to the first and third annular members 18a, 20 described above. Further, each flap 117 may not be attached to the structure that forms the compartment 119 (e.g., the third annular member 120) between the compartment 119 and the hole 145. A small gap or spacing is shown at this location in FIGS. 10 and 11. This arrangement can reduce the force(s) needed to open each flap 117.

Figure 13:
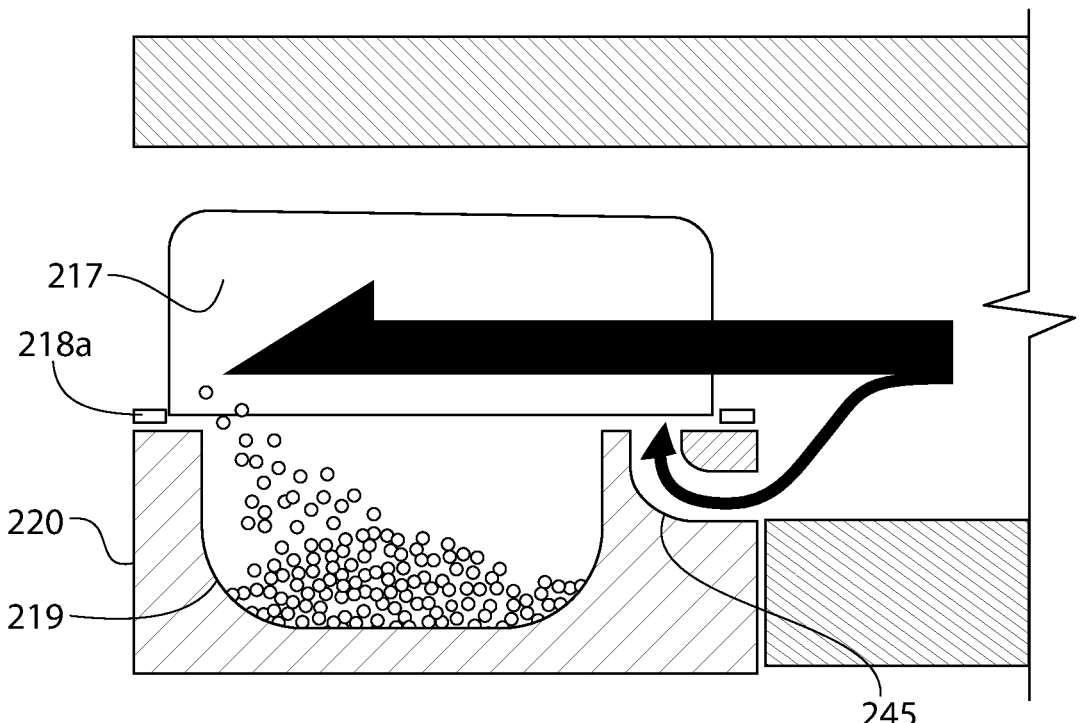
FIG. 13 is a cross-sectional side elevation view of a portion of an annular member according to an embodiment of the presently disclosed technology, wherein a flap is shown in an open position.
Figure 14:
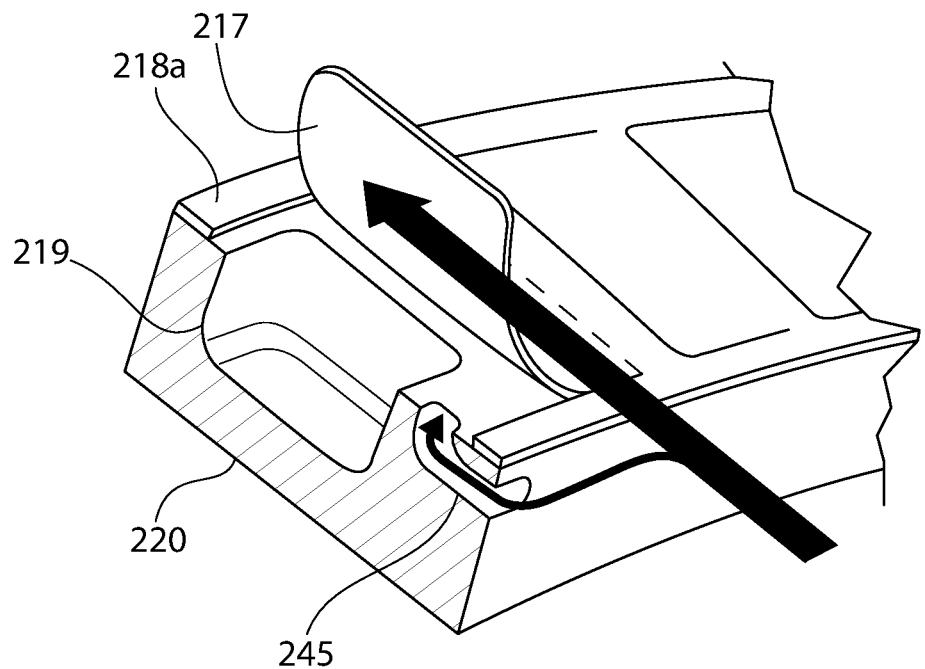
FIG. 14 is a perspective view of the features shown in FIG. 13.

FIGS. 13-14 show another embodiment of the presently disclosed technology. Similar or identical structure as between the embodiments of FIGS. 1-9 and FIGS. 13-14 is distinguished in FIGS. 13-14 by a reference number with a magnitude two hundred (200) greater than that of FIGS. 1-9. Description of certain similarities between the earlier embodiments and the embodiment of FIGS. 13-14 may be omitted herein for convenience and brevity only.

In the present embodiment, each hole 245 is a narrower, elongated passageway, which can have an "L" shape or include a 90 degree bend. The shape of each hole 245 can help increase the speed at which air is forced to flow through the respective hole 245, thereby increasing the force on the bottom surface of the respective flap 217. Each flap 217 can contact or extend radially beyond a portion of the structure that forms the respective compartment 219 and the hole 245 (e.g., the third annular member 220). Alternatively, as shown in FIG. 13, each flap 217 can contact the structure that defines the respective compartment 219, but can be free or spaced-apart from the entire structure that defines the respective hole 245. In the closed position, each flap 217 can cover one end (e.g., a downstream end) of the passageway formed by the respective hole 245.

Figure 15:
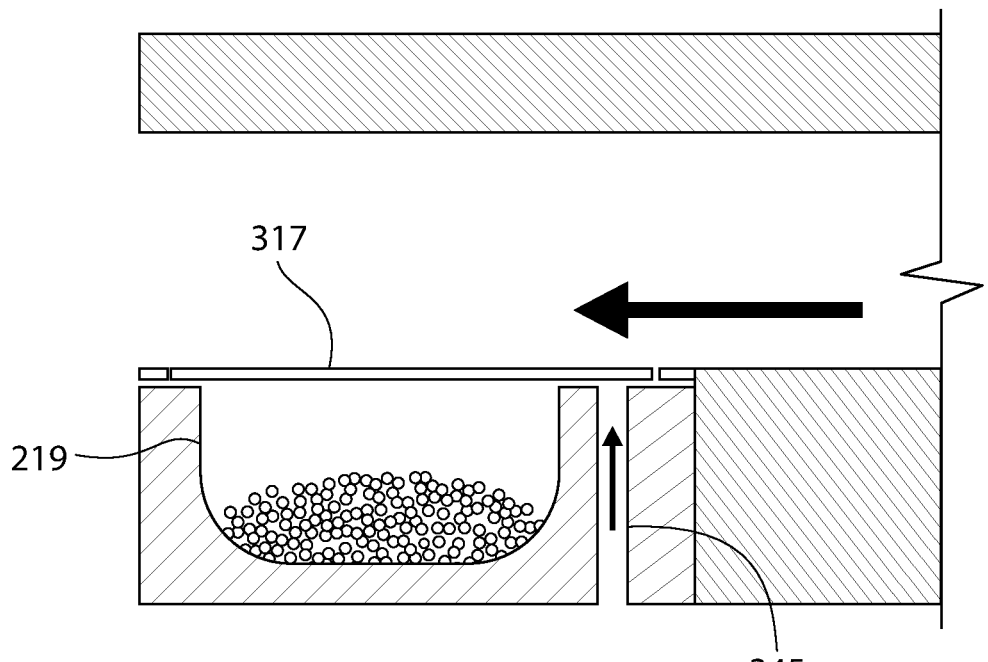
FIG. 15 is a cross-sectional side elevation view of a portion of an annular member according to an embodiment of the presently disclosed technology, wherein a flap is shown in a closed position.
Figure 16:
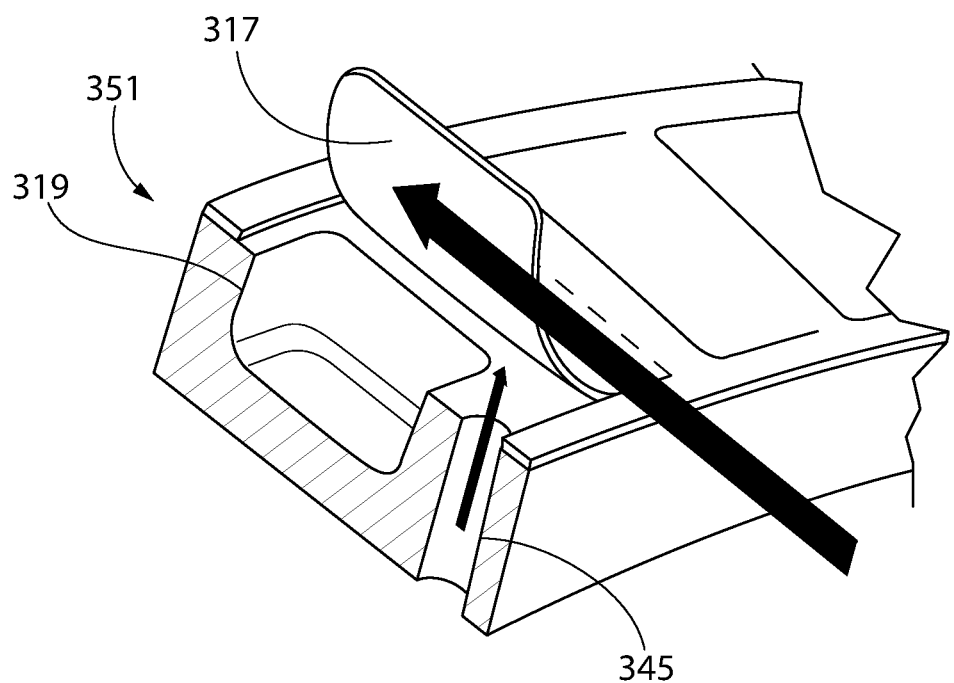
FIG. 16 is a perspective view of the features shown in FIG. 15, wherein the flap is shown in an open position.

FIGS. 15-16 show another embodiment of the presently disclosed technology. Similar or identical structure as between the embodiments of FIGS. 1-9 and FIGS. 15-16 is distinguished in FIGS. 15-16 by a reference number with a magnitude three hundred (300) greater than that of FIGS. 1-9. Description of certain similarities between the earlier embodiments and the embodiment of FIGS. 15-16 may be omitted herein for convenience and brevity only.

In the present embodiment, each hole 345 is a passageway that extends entirely perpendicularly to a plane defined by a top surface of the respective flap 317. As a result, the airflow through each hole 345 is perpendicular to the airflow across the top of the respective flap 317. The location of each hole 345 is not limited to being downstream of the respective compartment 319. For example, the hole 345 shown in FIG. 15 could be to the left (instead of the right) of the compartment 319. In addition, the flaps 317 are not limited to being formed or cut from a single first annular member. Instead, each flap 317 can be a separate and discrete component, and can be attached to the annular member 351 in any of a variety of ways, such as an adhesive.

Figure 17:
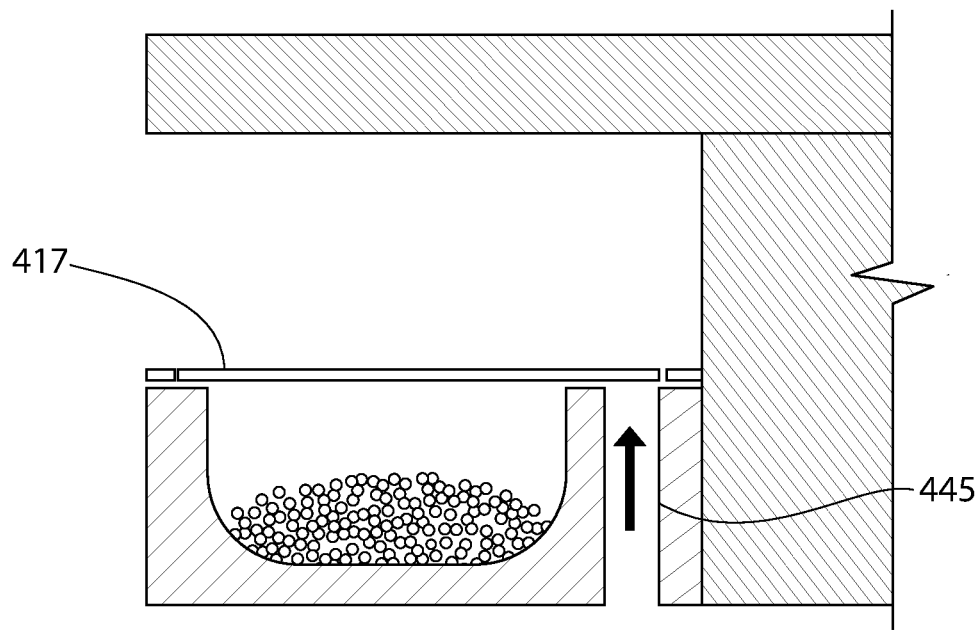
FIG. 17 is a cross-sectional side elevation view of a portion of an annular member according to an embodiment of the presently disclosed technology, wherein a flap is shown in a closed position.
Figure 18:
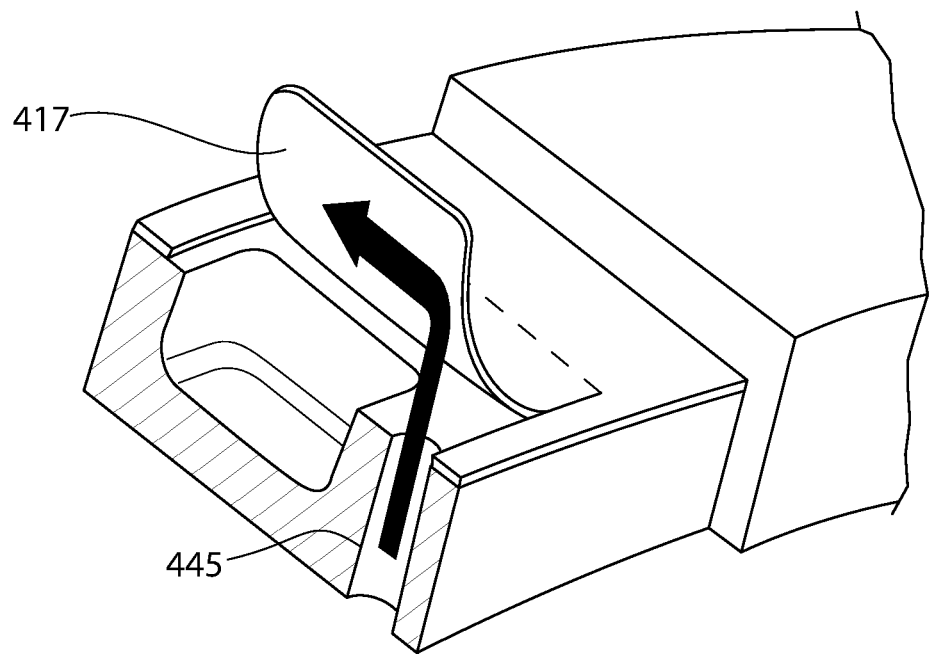
FIG. 18 is a perspective view of the features shown in FIG. 17, wherein the flap is shown in an open position.

FIGS. 17-18 show another embodiment of the presently disclosed technology. Similar or identical structure as between the embodiments of FIGS. 1-9 and FIGS. 17-18 is distinguished in FIGS. 17-18 by a reference number with a magnitude four hundred (400) greater than that of FIGS. 1-9. Description of certain similarities between the earlier embodiments and the embodiment of FIGS. 17-18 may be omitted herein for convenience and brevity only.

In contrast to the earlier embodiments, the present embodiment utilizes only a single airflow path (e.g., beneath each flap 417) to open each flap 417. In particular, in the present embodiment, there is no additional airflow path that only travels above each flap 417. Although the hole 445 is shown as being perpendicular to the top surface of the respective flap 417, the hole 445 could have an alternative shape or dimensioning, such as those described earlier.

Figure 19:
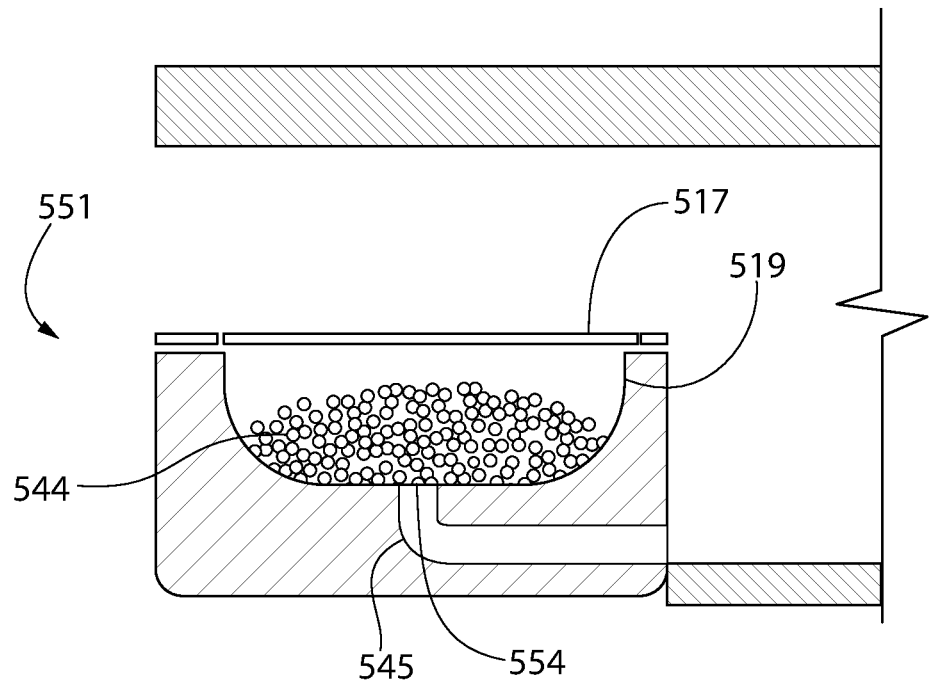
FIG. 19 is a cross-sectional side elevation view of a portion of an annular member according to an embodiment of the presently disclosed technology, wherein two flaps of the annular member are shown in a closed position.
Figure 20:
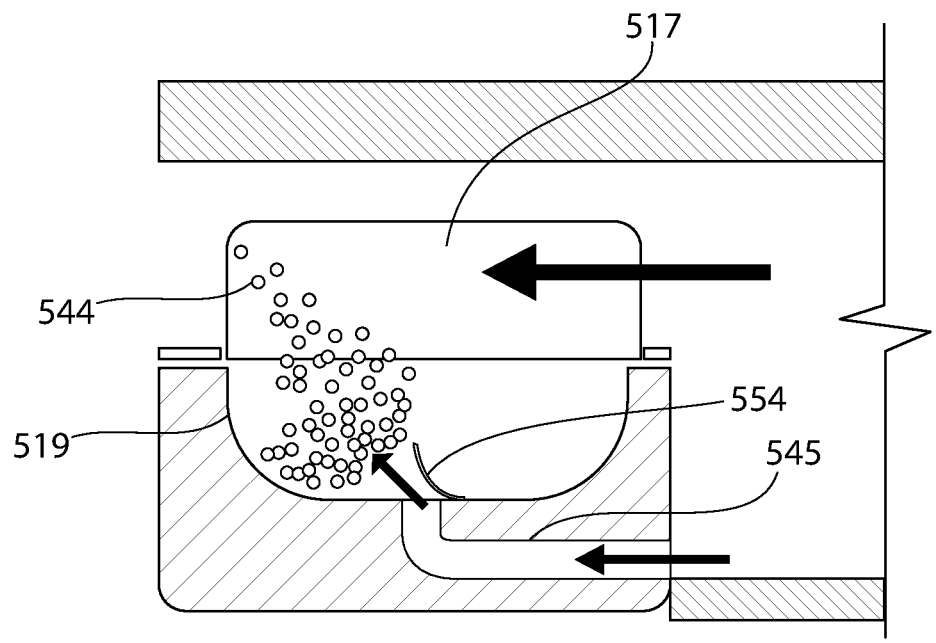
FIG. 20 is another cross-section side elevation view of the features shown in FIG. 21, wherein each flap is shown in an open position.
Figure 21:
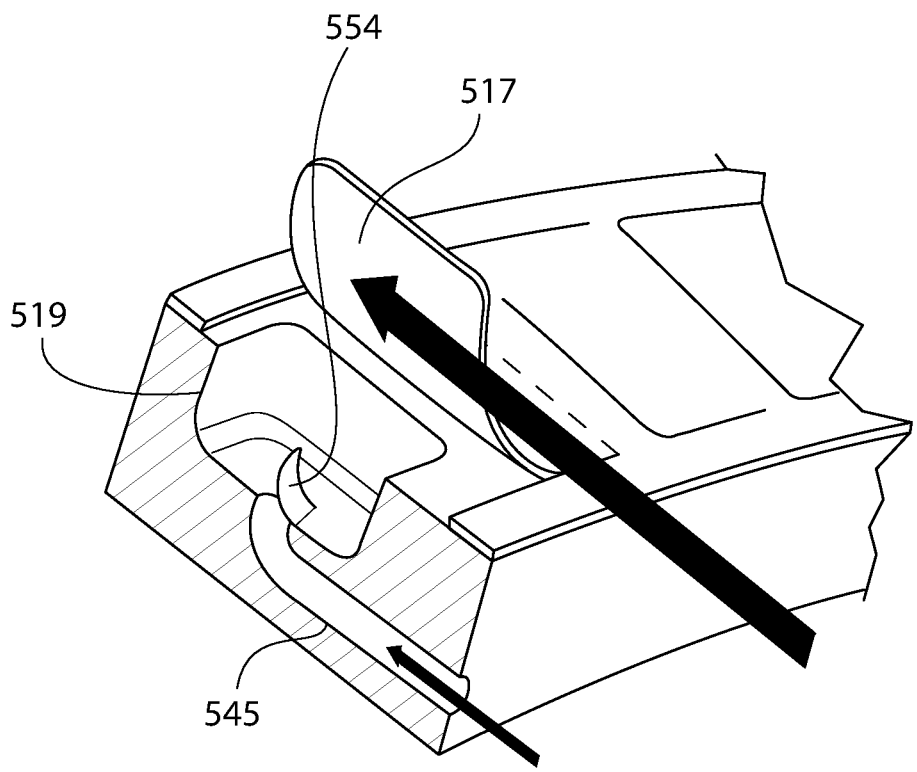
FIG. 21 is a perspective view of the features shown in FIG. 20.

FIGS. 19-21 show another embodiment of the presently disclosed technology. Similar or identical structure as between the embodiments of FIGS. 1-9 and FIGS. 19-21 is distinguished in FIGS. 19-21 by a reference number with a magnitude five hundred (500) greater than that of FIGS. 1-9. Description of certain similarities between the earlier embodiments and the embodiment of FIGS. 19-21 may be omitted herein for convenience and brevity only.

A distinguishing feature of the present embodiment is that the annular member 551 includes a first flap 517 at a top of each compartment 519 and a second flap 554 at a bottom of each compartment 519. At least a portion of the second flap 554 can be secured (e.g., via adhesive) to or integrally formed with an interior of the respective compartment 519, and another portion of the second flap 554 can be movable with respect to the interior of the respective compartment 519. The powder 544 is located between an interior surface of the second flap 554 and an interior surface of the first flap 517.

Another distinguishing feature of the present embodiment is that the hole 545 leads into the interior of the respective compartment 519, as opposed to adjacent the respective compartment 519 as described in the earlier embodiments. Air traveling through the hole 545 pushes upwardly on an exterior surface of the second flap 554 until the air flow pushes the second flap 554 into the compartment 519, thereby pushing the powder 544 toward the first flap 517 and out of the compartment 519 after the first flap 517 is opened.

In one embodiment, the first flap 517 can be opened as a result of the force created by the air flow traveling through the hole 545. In an alternative embodiment, the first flap 517 can be opened by a combination of a pressure differential generated by an air stream that travels across a top of the flap 517, and the force created by the air flow traveling through the hole 545. In either case, the air flow moves the first and second flaps 517, 554 in the same direction when opening both the first and second flaps 517, 554.

While the presently disclosed technology has been described in detail and with reference to specific examples thereof, it will be apparent to one skilled in the art that various changes, omissions and modifications can be made therein without departing from the spirit and scope thereof. It is understood, therefore, that the presently disclosed technology is not limited to the particular embodiments disclosed, but it is intended to cover modifications within the spirit and scope of the present presently disclosed technology as defined by the appended claims.

What is claimed is:

1. An inhaler for facilitating inhalation of dry powder, the inhaler comprising:
   a body defining an interior space and including a mouth piece; and
   at least one annular member within the interior space and rotatable with respect to the mouth piece, the at least one annular member including a plurality of compartments and a plurality of flaps, each flap being associated with at least one of the compartments, each compartment defining a cavity configured to hold dry powder and including an opening configured to release the dry powder when the flap is moved from a closed position to an open position, each flap covering at least the opening of one of the compartments and including an extension extending beyond the associated compartment or compartments,
   wherein at least a portion of the extension of each flap is configured to be exposed to an airflow acting on an underside of the extension when the flap is in the closed position, such that the airflow is configured to move the flap from the closed position to the open position acting on the underside of the extension of each flap.

2. The inhaler of claim 1, wherein the at least one annular member includes a plurality of conduits, each conduit being associated with one of the compartments, each flap covering at least a portion of one end of the associated conduit when the flap is in the closed position.

3. The inhaler of claim 2, wherein at least a portion of the underside of each flap faces the associated conduit.

4. The inhaler of claim 3, wherein air travels through at least one of the plurality of conduits to facilitate movement of the associated flap from the closed position to an open position.

5. The inhaler of claim 1, wherein the body contains desiccant.

6. The inhaler of claim 1, wherein the body includes three components, at least one of the components being formed of a low moisture vapor transmission (LMVT) rate material.

7. An inhaler for facilitating inhalation of dry powder, the inhaler comprising:
   a body defining an interior space and including a mouth piece; and
   at least one member within the interior space of the body, the at least one member including an i) opening extending therethrough to the mouth piece, ii) at least one compartment, iii) at least one flap, and iv) at least one conduit, the at least one compartment defining a cavity configured to hold dry powder and including a compartment opening configured to release the dry powder when the at least one flap is moved from a closed position to an open position, the at least one conduit corresponding to or being next to the at least one compartment, the at least one flap covering at least a portion of one end of the at least one conduit when the at least one flap is in the closed position,
   wherein air travels through the at least one conduit to facilitate movement of the at least one flap from the closed position to an open position, and
   wherein the at least one compartment includes a plurality of compartments, the at least one flap includes a plurality of flaps, and the at least one conduit includes a plurality of conduits.

8. The inhaler of claim 7, wherein the at least one member is at least one annular member that is rotatable with respect to the mouth piece.

9. The inhaler of claim 7, wherein each flap is associated with one of the compartments and each conduit is associated with one of the compartments.

10. The inhaler of claim 7, wherein the at least one flap includes a first flap and a second flap, the first flap configured to close a first opening of at least two openings, the second flap being configured to close a second of the at least two openings.

11. The inhaler of claim 10, wherein the first opening is larger than the second opening.

12. The inhaler of claim 10, wherein the first opening is located at a bottom surface of the at least one compartment.

13. The inhaler of claim 7, wherein an outer periphery of the at least one member includes teeth.

14. The inhaler of claim 7, wherein the at least one member includes a first annular member and at least a second annular member, the second annular member being bonded to the first annular member.

15. An inhaler for facilitating inhalation of dry powder, the inhaler comprising:
    a body defining an interior space and including a mouth piece; and
    at least one member within the interior space of the body, the at least one member including at least one compartment, at least one flap, and at least one conduit, the at least one compartment defining a cavity configured to hold dry powder and including an opening configured to release the dry powder when the at least one flap is moved from a closed position to an open position, the at least one flap covering at least a portion of one end of the at least one conduit when the at least one flap is in the closed position,
    wherein the at least one flap includes a first flap and a second flap, the first flap configured to close a first opening of at least two openings, the second flap being configured to close a second of the at least two openings, and
    wherein air flowing proximate the at least one compartment moves the first and second flaps in the same direction.

16. A method of administering dry power medicament, the medicament contained in an inhaler, the inhaler including a body defining an interior space and including a mouth piece, the inhaler further including at least one member within the interior space of the body, the at least one member including an i) opening extending therethrough to the mouth piece, ii) at least one compartment, iii) at least one flap, and iv) at least one conduit, the at least one compartment defining a cavity containing dry powder and including a compartment opening configured to release the dry powder when the at least one flap is moved from a closed position to an open position, the at least one conduit corresponding to or being next to the at least one compartment, the at least one flap covering at least a portion of one end of the at least one conduit when the at least one flap is in the closed position, the method comprising:
    inhaling or evacuating air from within the interior space of the body through the mouth piece, thereby causing air to move through the at least one conduit and lift the at least one flap, and
    wherein the at least one compartment includes a plurality of compartments, the at least one flap includes a plurality of flaps, and the at least one conduit includes a plurality of conduits.

17. The method of claim 16, wherein lifting of the at least one flap by the air moving through the at least one conduit allows at least some of the dry power to pass through the mouth piece.

18. The method of claim 16, wherein the at least one member is at least one annular member that is rotatable with respect to the mouth piece.

19. The method of claim 16, wherein the at least one compartment includes a plurality of the compartments and the at least one flap includes a plurality of the flaps, each flap being associated with at least one of the compartments, each flap covering the opening of at least one of the compartment and including an extension extending beyond the associated compartment or compartments, and wherein at least a portion of the extension of each flap is configured to be exposed to an airflow acting on an underside of the extension.

20. A method of administering dry powder medicament, the medicament contained in an inhaler, the inhaler including a body defining an interior space and having a mouth piece, the inhaler further including at least one annular member within the interior space and rotatable with respect to the mouth piece, the at least one annular member including a plurality of compartments and a plurality of flaps, each flap being associated with at least one of the compartments, each compartment defining a cavity configured to hold dry powder and including an opening configured to release the dry powder when the flap is moved from a closed position to an open position, each flap covering at least the opening of one of the compartments and including an extension extending beyond the associated compartment or compartments, at least a portion of the extension of each flap is configured to be exposed to an airflow acting on an underside of the extension, the method comprising:
    inhaling or evacuating air from within the interior space of the body through the mouth piece, thereby causing the airflow to act on the underside of the extension of one of the plurality of flaps when the respective flap is in the closed position to move the respective flap from the closed position to the open position.

* * * * *